(12) United States Patent
Ruohonen et al.

(10) Patent No.: US 9,375,585 B2
(45) Date of Patent: Jun. 28, 2016

(54) MAGNETIC STIMULATION DEVICE AND METHOD

(75) Inventors: Jarmo Ruohonen, Vantaa (FI); Jari Karhu, Kuopio (FI)

(73) Assignee: NEXSTIM OY, Helsinki (FI)

( * ) Notice: Subject to any disclaimer, the term of this patent is extended or adjusted under 35 U.S.C. 154(b) by 0 days.

(21) Appl. No.: 13/378,955

(22) PCT Filed: Jun. 17, 2009

(86) PCT No.: PCT/FI2009/050524
§ 371 (c)(1),
(2), (4) Date: Dec. 20, 2011

(87) PCT Pub. No.: WO2010/146220
PCT Pub. Date: Dec. 23, 2010

(65) Prior Publication Data
US 2012/0101366 A1   Apr. 26, 2012

(51) Int. Cl.
*A61F 2/02*    (2006.01)
*A61B 17/12*   (2006.01)
*A61N 2/00*    (2006.01)
*A61N 2/02*    (2006.01)

(52) U.S. Cl.
CPC .............. *A61N 2/004* (2013.01); *A61N 2/006* (2013.01); *A61N 2/02* (2013.01)

(58) Field of Classification Search
CPC .......... A61N 2/004; A61N 2/006; A61N 2/02
USPC ............ 600/14, 300, 411, 427, 437, 544, 546
See application file for complete search history.

(56) References Cited

U.S. PATENT DOCUMENTS

| 6,061,593 | A  |   | 5/2000 | Fischell et al. |
| 6,849,040 | B2 | * | 2/2005 | Ruohonen et al. ............. 600/14 |
| 2004/0111127 | A1 | * | 6/2004 | Gliner ............................. 607/45 |
| 2004/0122702 | A1 | * | 6/2004 | Sabol et al. ..................... 705/2 |
| 2005/0107654 | A1 | * | 5/2005 | Riehl .............................. 600/9 |

(Continued)

FOREIGN PATENT DOCUMENTS

| WO | WO 01/28622 A2 | 4/2001 |
| WO | WO 2005/051479 A2 | 6/2005 |
| WO | WO 2009/132855 A2 | 11/2009 |

OTHER PUBLICATIONS

G. Hajcak, C. Molnar, M.S. George, K. Bolger, J. Koola, Z. Nahas, "Emotion facilitates action: A transcranial magnetic stimulation study of motor cortex excitability during picture viewing," Psychophysiology, Jan. 2007, vol. 44, pp. 91-97.*

*Primary Examiner* — Charles A Marmor, II
*Assistant Examiner* — Joshua D Lannu
(74) *Attorney, Agent, or Firm* — Birch, Stewart, Kolasch & Birch, LLP

(57) ABSTRACT

The present publication discloses a device and method for generating magnetic pulses and directing them to brain. The device in accordance with the invention comprises means (15) for generating short, high energy current pulses (18), means (7) for controlling amplitude (16) of the current pulses (18), means (1) for generating high energy electromagnetic field stimulation pulses from the current pulses (18) and directing them to brain, and means (6, 14) for measuring biologic responses to the stimulation pulses. In accordance with the invention the device includes means (7) for creating such a pulse sequence (17) of electromagnetic pulses where the amplitude (18) varies irregularly.

45 Claims, 6 Drawing Sheets

(56) References Cited

U.S. PATENT DOCUMENTS

| | | |
|---|---|---|
| 2006/0015153 A1 | 1/2006 | Gliner et al. |
| 2007/0083097 A1* | 4/2007 | Fujiwara et al. .............. 600/407 |
| 2007/0173904 A1 | 7/2007 | Pilla |
| 2007/0260107 A1* | 11/2007 | Mishelevich et al. ........... 600/14 |
| 2007/0288072 A1* | 12/2007 | Pascual-Leone et al. ....... 607/88 |
| 2009/0082690 A1 | 3/2009 | Phillips et al. |
| 2010/0113959 A1* | 5/2010 | Pascual-Leone et al. ..... 600/544 |

* cited by examiner

MAGNETIC STIMULATION DEVICE AND METHOD

FIELD OF THE INVENTION

The present invention relates to the non-invasive stimulation of the human brain according to pre-determined pulses for the purpose of inferring information related to the ability of the brain and its descending pathways to conduct neuronal signals. In particular, this invention relates to fast pulse sequences that combined with detected changes in biological measurements provide measurement information faster and more reliably than would otherwise be possible. In particular, the present invention relates to what is stated in the preamble portion of the independent claims.

PRIOR ART

Transcranial magnetic stimulation (TMS) offers a method to stimulate the motor areas of the human brain. Stimulation of the primary representation area of a muscle may result in activation of the corticospinal neuronal pathways that originate from the cerebral cortex and create a pathway to the spinal cord, from where neuronal signals are carried by peripheral nerves to muscles and eventually trigger activation of muscles. The muscle twitches can be detected quantitatively using surface electromyograph (EMG). These EMG responses to brain stimulation are called motor-evoked potentials or MEP's.

TMS has been used to examine the function of the cerebral cortex and the corticospinal pathways. The method can provide information that helps medical personnel in their decisions leading to diagnosis, prognosis and therapy. A wide range of medical specialties are either using or exploring the use of TMS; presently TMS is most beneficial in neurology, neurosurgery and psychiatry, and in neuroscientific research. Literature on TMS includes many different methods for the examination of the relationship between the TMS stimulus and the responses elicited by the stimulus. The relationship can then be used to evaluate and examine the function of the brain region stimulated and its various neuronal connections. A typical TMS measurement starts with determination of the threshold TMS intensity that elicits MEP's to 50% of the TMS pulses. The value determined is called the motor threshold (MT), and can be determined for muscles that are either at rest or at least partially pre-activated. It is to be noted that the value is an estimate, because exact determinatation would in theory require an infinite number of stimulus pulses. The motor threshold is normally different for different target muscles and may be different for the left and right side of the body. Literature also reports great individual differences in the motor threshold (Mills and Nithi, Muscle and Nerve, 20: 570-576, 1997; Pitcher et al., J Physiology, 542: 605-613, 2003).

The motor threshold reflects the excitability of the motor cortex and the corticospinal pathways. TMS offers also possibilities for other types of measurements that reflect the excitability, but also other characteristics of the central nervous system. The individual motor threshold forms the basis for adjusting the stimulation intensity in nearly all of these other examinations. A frequent measurement is to determine the mean size and latency of the MEP responses to one fixed stimulus intensity, where the stimulus is 10-20% stronger than the estimated motor threshold. The mean size and latency reflect the capacity of the cerebral cortex and the corticospinal pathway to conduct neuronal signals. Studies normally compare responses in the left and right side of the body. Another standard measurement is to stimulate at different intensities and observe the change in the size of the responses elicited. This is known as the determination of the input-output curve, also known in literature as the recruitment curve. These parameters may provide information that complements diagnostic decision-making and monitoring of the progress of a disease or recovery from the disease. The information provided by such measurements can aid medical personnel when performing diagnosis or prognosis or when treating a disease. For instance, a changed MT may be observed in the hand muscles of patients who have had a stroke that affects the hand functioning. Likewise, the recruitment curve may change during the course of a disease, including changes in the slope and the area under the curve.

A frequently used protocol in using TMS is to first hold the coil in different locations above the head, deliver stimulus pulse to each location, and observe the elicited motor evoked responses from one or more muscles. The coil location associated to the strongest responses is then repeated.

Pulses of different intensity are given according to published protocols to determine the MT (e.g., Rossini et al. Electroenceph. Clin. Neurophysiol.m 91:79-92, 1994), Awiszus F, Suppl. Clin Neurophysiol. 56: 13-23, 2003). These are iterative algorithms where the user selects the intensity of the next pulse based on the MEP response to the previous stimulus. Typically, after a non-responding stimulus, a stimulus of higher intensity is delivered, and vice versa. At least in principle, it is possible to construct a feedback loop between TMS and EMG devices, where the system is computerized and iteratively adjusts the next stimulus intensity without user input. Such method is discussed, e.g., in publication U.S. Pat. No. 7,104,942.

It is frequent to record MEP values at stimulus intensity corresponding to 1.1 to 1.2 times the intensity of motor threshold; mean value of several response strengths is normally determined. Next, it is frequent to select several intensity levels that also are referenced to the Motor Threshold, for example, 0.8, 0.9, 1.0, 1.1, and 1.2 times the pre-defined Motor Threshold intensity. Several stimuli are given at of these each intensity in a row while recording the MEP responses. The responses are analyzed and the mean of the responses is plotted with relation to the stimulus intensity.

DISADVANTAGES OF THE PRIOR ART

The known protocols require the Motor Threshold (MT) intensity to be determined prior to measuring other values. MT is determined by following written or computerized iterative protocols which tell to the user the next intensity to apply, based on the results of the previous one or more stimuli. A disadvantage of such protocols is that MEP's are known to have great variability, which greatly affects the results of iterative processes. Normally, on the order of 10 to 100 pulses are needed to determine the MT reliably; accuracy of the determination improves with number of iterations. An iterative MT determination is prone to human mistakes and sensitive to errors in the measurement. One mistake or error can affect the path of the iteration significantly and lead to erroneous result especially if the number of stimulus pulses is low. It is beneficial to use low number of pulses to reduce the length of the examinations.

The necessity to use MT value as the starting point for other TMS examinations adds to the number of stimulus pulses that need to be given, which from its part lengthens the examination sessions. Long examination duration affects negatively the reliability and repeatability of the results. MEP's are affected by changes in alertness, vigilance, drowsiness, etc., of the subject or patient. Assessment of the changes in the measured parameters during the course of a disease or recovery from a disease is greatly limited by the resulting variability in the measured results. It is important to conduct the examinations under stable conditions, and lengthy examinations are unfavorable.

There are also other disadvantages. To determined the Recruitment curve (discussed above), it is first necessary to calculate the intensity which is given as percentage value (say 20%) above the MT, and then stimulate several times (e.g., 10) applying that intensity and finally average the size of the responses to each of the stimulus intensities. Present-day methods apply pulses of equal intensity in groups. The average response to each intensity value is calculated and used to estimate the input-output relationship. This approach has several disadvantages. First, TMS responses are known to be conditioned by the pulses given previously, especially when the inter-stimulus interval is shorter than 2-5 seconds. Additionally, intensity of the stimulus pulse also is known to affect the MEP response to the following pulse or pulses. Therefore, the application of the stimulus intensities in groups of equal intensity value will create an input-output curve which has artefactual bias. Application of similar intensities several times in a row introduces additional errors in the interpretation of the responses because the brain habituates. The subject may also learn to expect a stimulus, which is known to affect the size of the MEP responses.

In summary, the known methods have several drawbacks:
The time required for the stimulation measurement is lengthy as it consists of several parts.
Number of pulses is relatively high compared to the information generated.
MT needs to be determined prior to running other measurements, excluding all flexibility from the procedure.
Iterative MT determination is prone to human mistakes and sensitive to errors in the measurement. One mistake or error can affect the path of the iteration significantly and lead to erroneous result especially if the number of stimulus pulses is low.
Lengthy exam time can lead for the MT to have been determined under different conditions than the rest of the measurements. This leads to inaccurate and poor-quality information.
Problem that MEP values change a lot, and lead to poor estimation of MT and recruitment curve.

AIM OF THE INVENTION

It is the aim of this invention to reduce or remove at least some of the disadvantages of the prior art and to provide method and equipment that provides faster and more reliable measurements using transcranial magnetic stimulation.

SUMMARY OF THE INVENTION

The invention is based on stimulating the brain using a pre-determined pulse sequence and apparatus capable of delivering such stimuli using transcranial magnetic stimulation technique. The method eliminates the need of determining a person's individual stimulation threshold intensity before it is possible to perform other types of measurements. The invention allows for faster determination of selected TMS response values while using less number of stimulus pulses. The invention can comprise an apparatus that can deliver sequences of pulses with pre-set intervals and with irregularly varying intensity.

More specifically, the device according to the invention is characterized by what is stated in the characterizing portion of claim 1.

For its part, the method according to the invention is characterized by what is stated in the characterizing portion of independent method claim 24.

Advantages

In the present invention, the TMS examinations can be faster. One single pulse sequence can be used to acquire data that would otherwise require applications of many more pulses. In particular the invention can be used to combine the recording of MT, Recruitment curve and MEP average values into one single pulse sequence instead of several required in the present techniques. Also, the invention improves significantly the reliability and repeatability of the TMS measurements. Application of pre-programmed and irregular TMS pulse series removes problems related to iterative searches used in the earlier methods; it also removes problems related to the different interpretations of MEP's and iterative processes due to intra-operative differences. In other words, the invention increases the objectivity of the TMS measurements. Additionally, the application of the irregular sequences described in this invention enable automatic measurements of selected TMS parameters that reflect the characteristics of the central nervous system.

In the following the invention is described with references to the accompanying drawings, in which:

DESCRIPTION OF THE PREFERRED EMBODIMENTS

The following terms with reference numbers will be used in connection with this application:

TABLE 1

List of reference numbers

| Reference number | Part |
|---|---|
| 1 | TMS coil |
| 2 | Digitizer pen |
| 3 | Head tracker |
| 4 | Patient chair |
| 5 | Foot switch |
| 6 | EMG device (amplifier and electrodes) |
| 7 | Controlling computer |
| 8 | Position sensor power supply unit |
| 9 | Medical isolation transformer |

TABLE 1-continued

List of reference numbers

| Reference number | Part |
|---|---|
| 10 | EMG device power supply |
| 11 | Display |
| 12 | Position sensor |
| 13 | Coil tracker |
| 14 | Electrodes |
| 15 | TMS device |
| 16 | TMS pulse amplitude |
| 17 | TMS pulse sequence |
| 18 | TMS pulse |
| 19 | Interstimulus interval (ISI) |
| 20 | Pulse duration |

Figure 1:
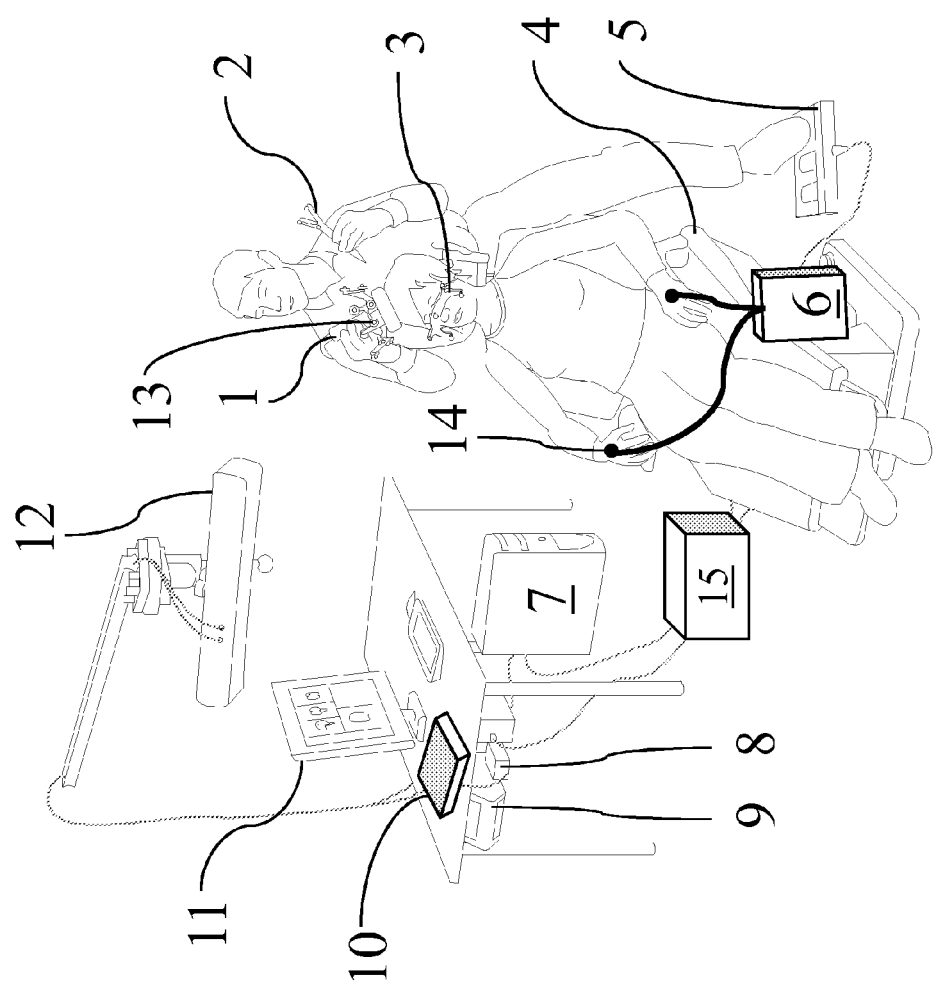
FIG. 1 shows a schematic overview of an environment in which TMS treatments are applied.

The required equipment according to the invention are the TMS device, TMS coil, data processor and equipment for measuring biosignals, illustrated in FIG. 1. For the purpose of clarity the biosignal unit in the FIG. 1 is drawn as an EMG device. The data processor 7 can be an integrating computer or also distributed software that resides in one or more physical locations such as embedded software and PC software. The data processor includes a list of pulse intensities in the pulse sequence and information about the timing of the pulses. The data processor also oversees the appropriate delivery of the requested sequence of pulses by the TMS devices.

The auxiliary equipment illustrated in FIG. 1 includes cables and transformers 9. The EMG device illustrated comprises an EMG amplifier 6, a power supply 10 and electrodes 14. The patient is equipped with electrodes 14 of an EMG amplifier 6, which electrodes 14 are attached to the part of the patient being the object of interest, typically over the belly of one or more muscles. The EMG electrodes 14 record electrical potentials related to muscle activation. The recording of the signals can be time-locked to the TMS pulses related to record TMS evoked muscle responses. An EMG amplifier 6 is located adjacent to the patient chair 4 and amplifies the signal of the EMG electrodes 14. The biosignals are then digitized and fed to a processor or computer for display and analysis. The equipment can also detect other types of biosignals, such as EEG signals or muscle force responses, while EMG measurements are the most probable application. The EMG amplifier 6 is powered by an EMG power supply 10. The short magnetic field pulses are given with a TMS coil 1 where the pulse has a duration of approximately 50 microseconds to 2 milliseconds, advantageously from 100 to 500 microseconds.

The TMS coil 1 is operated with a trigger switch 5, which can be a foot switch, which triggers the given pulse or the execution of the entire pulse sequence. The foot switch 5 is connected to the TMS device 15, which fires a pulse through the TMS coil 1.

Figure 2:
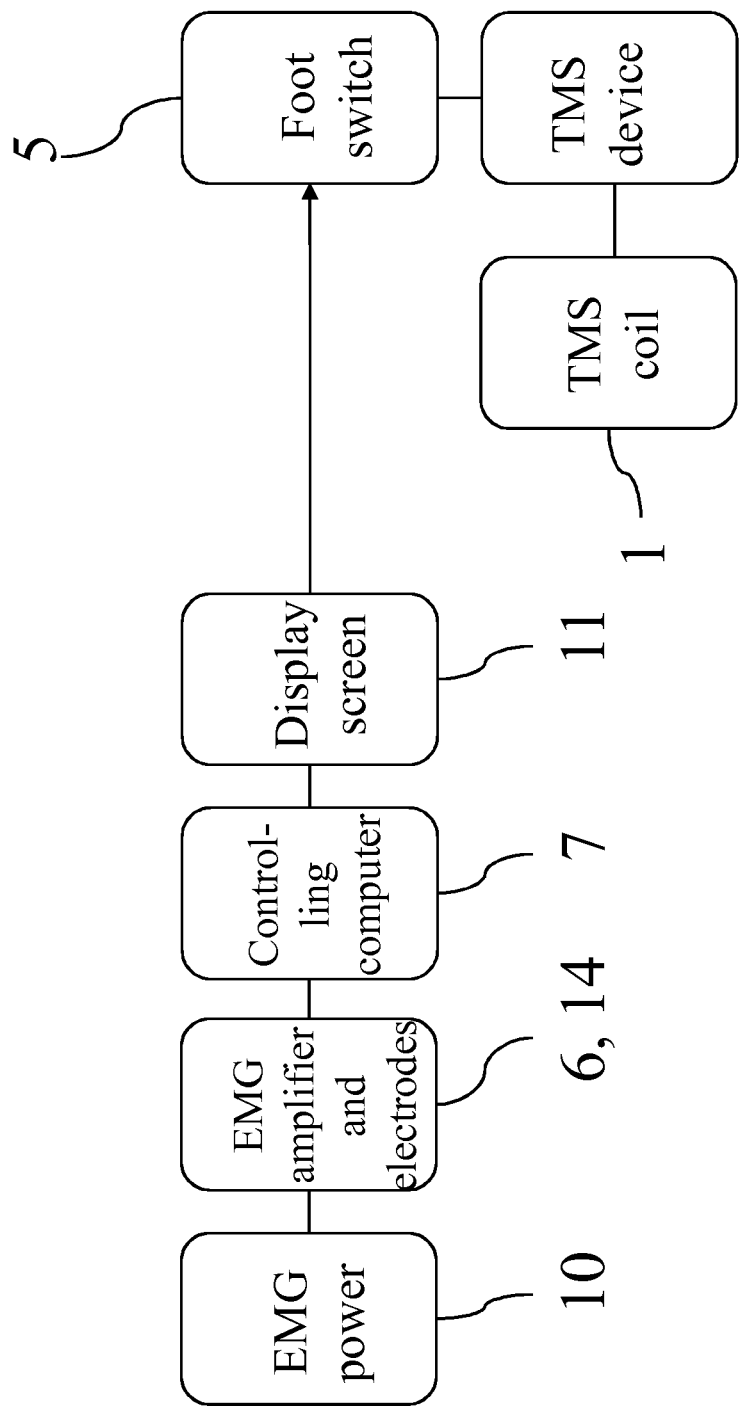
FIG. 2 shows a block diagram of a TMS arrangement according to prior art.

The arrangement of the prior art is illustrated as a block diagram in FIG. 2. The major components of a TMS examination system can be set up as separate or integreated entities so that the operation of the system as a whole is triggered by the firing of the TMS device.

Figure 3:
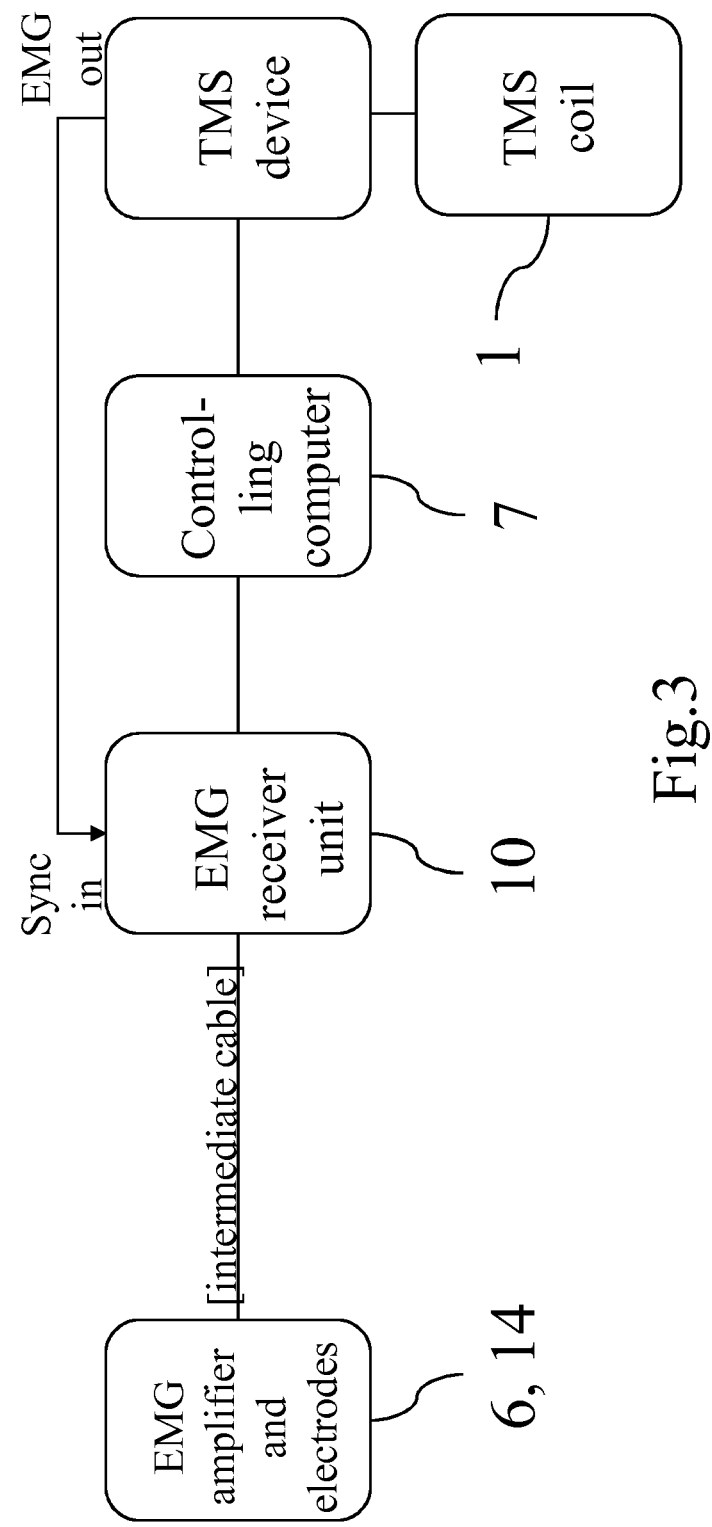
FIG. 3 shows the connections between TMS and EMG devices and a connecting computer.

Referring now to FIG. 3, the EMG signal is fed from the EMG amplifiers 6 to a signal processor unit (typically a controlling computer 7) via a USB cable, and the selected channel or channels are analyzed immediately. As is also apparent from FIG. 3, the EMG receiver unit 10, the controlling computer 7 and the TMS device 15 are linked together. The linkage can be provided by using, e.g. USB lines, wireless communication, or TTL level synchronization signals.

When the operator presses the foot pedal or otherwise triggers a stimulus pulse, the control computer 7 sends a trigger signal to the TMS device 15. A synchronization signal is passed to the EMG device either directly by the computer or from the TMS device 15 so that the EMG signals can be related to the timing of the TMS pulse. The EMG can thereby be synchronized to the TMS pulses. The signal processor unit includes means for forming a signal or message that includes the stimulus intensity and the stimulus response characteristics and passes that sends messages to another signal processor unit or to the same or different program that is running in the same signal processor unit.

Calculations are performed in the signal processor unit that forms graphical or numeric relationship between the stimuli in the sequence and the responses, and they will be outputted on the display.

The TMS device 15 can be equipped with a means for localization of the coil with respect to individual brain's anatomical structures acquired using MR imaging. In this embodiment, the TMS coil is equipped with a coil tracker 13. The coil tracker 13 provides position information about the location and alignment of the TMS coil 1. A position sensor 12, located so that it is within unrestricted view of the trackers 3, 13, collects the position information of the head and coil trackers 3, 13 and is powered by a position sensor power supply unit 8. A preferable location for the position sensor 12 is the ceiling. A digitizer pen 2 is used for co-registering the live head with MR images of the same head. The computer then collects all localization information and can display to the user in real-time the exact location of the coil over the head and the stimulus distribution in the brain as an overlay on the MR images.

When a 3D localization system is used, there can be an additional signal to the control of the TMS triggering that controls the location of the coil with respect to the head. In studies that demand higher precision and repeatability, it is advantageous to have the coil at the same location during all TMS stimuli. Information from the 3D localization system can be used to decide whether a pulse is given or not, by determining whether the coil is in desired location and orientation. The limits vary with application. A typical limit could be less than 2-5 mm difference in the coil location and less than 5-10 degrees of difference in the coil's orientation.

Referring now to FIG. 1, according to another embodiment of the invention, the 3D localization system of the TMS equipment is used to provide additional information for controlling the administration of TMS pulses. The position information is preferably comparable numeric data. The process may be reinforced with an additional decision phase based on the position information of the 3D localization system. When preparing for a TMS session, limits for the patient's muscular activity can be set, in addition to limits set for the position of the TMS coil 1. When the foot switch 5 is activated, the predetermined position limits are compared with real-time position information provided by the 3D localization system. On the basis of the examples described above, it is obvious that within the scope of the invention, numerous solutions differing from the embodiments described above can be implemented. Furthermore, it is possible to gain a preferred embodiment of the invention by combining it with, for example, navigated TMS stimulation as disclosed in publication U.S. Pat. No. 6,827,681. Thus the invention is not intended to be restricted to apply to only the examples described above, but instead the patent protection should be examined to the full extent of the accompanying claims.

DESCRIPTION OF THE INVENTION

Figure 4:
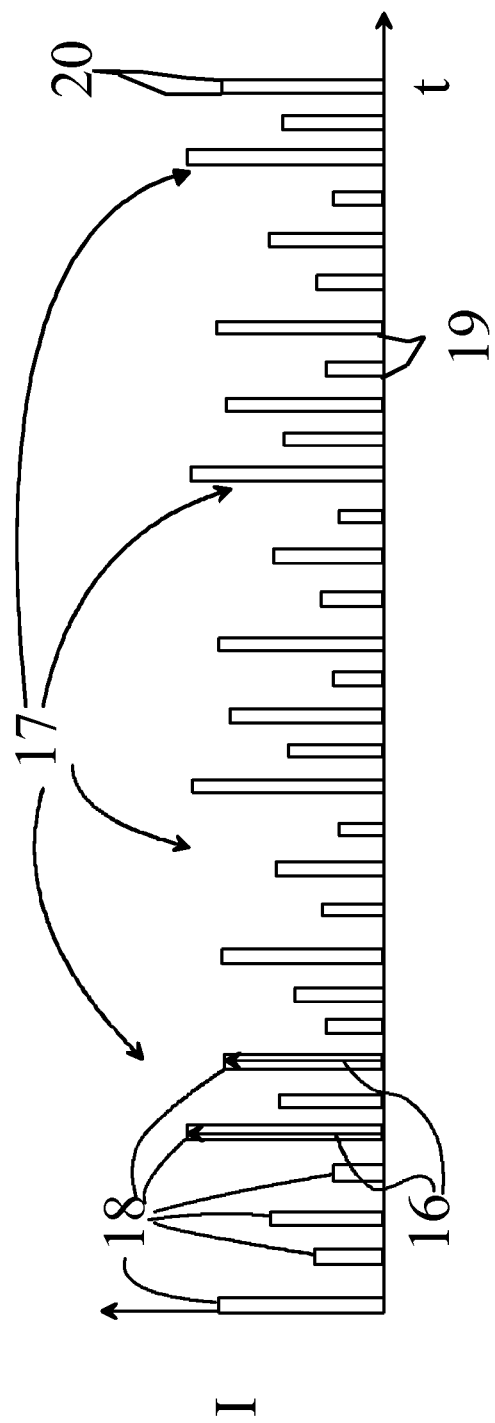
FIG. 4 shows a pulse sequence in accordance with the invention.

In accordance with FIG. 4 in the invention is used a sequence of pulses 17, which comprises pulses 18 with different amplitudes 16 (intensities). Typically the number of pulses is tens of pulses, e.g., 70 pulses. The amplitudes vary typically irregularly such a way that the subject and brain do not anticipate or learn to respond to the next pulse. One way to form irregularity is to use randomization. The randomization can be pseudo-randomization, that is, it does not need to be mathematically perfect. Especially systematic rising of falling trends of consequent pulses should be avoided. Typically the amplitudes are selected from predetermined amplitudes the number of which can for practical reasons be e.g. 5-10. The intensities may vary freely, in other words the amplitude may get any value between the minimum and maximum amplitude. These pulse sequences 17 are created typically by computer 7 such that the computer 7 includes the complete timing and amplitude of the pulses in the sequence in its memory. Alternatively, the computer 7 may include in its memory an algorithm for creating this sequence based on one or more parameters chosen by the user. These parameters may be e.g., the number of the pulses 18, ranges for the amplitude 16, time or range for the ISI 19, time or range for the duration of the pulse 20. The sequence may include repeating patterns, provided that the subject cannot learn to anticipate the next pulse, or the subject's brain does not habituate.

By a pulse sequence (or sequence of pulses) is meant in this application any irregular sequence of pulses with at least irregulary varying intensity. The intensity may have any value between 0% and 100% of the maximal output amplitude of the stimulator. The interstimulus interval (ISI) 19 between subsequent pulses in the sequence may in principle be anything between 0 and infinity. In practice, the shortest practical ISI is limited by the electronics generating the stimulus pulses and is about 1 ms. For physiological examinations where motor areas are stimulated and combined to peripheral EMG recordings, the lower value is limited by the refractoriness of the neurons and muscle fibers and neuronal feedback loops from periphery to the brain, to about ISI=100 ms. The upper limit for ISI is in practice limited by the maximal duration of the entire sequence, and thus the examination session. Considering that a pulse sequence would normally include from 10 to 200 pulses, the ISI value should preferentially be less than 20 seconds to limit the duration of the examination. A pulse sequence for very rapid measurement could, e.g., have ISI=200 ms and have 50 pulses in 10 different intensities. Another example is a fast measurement of the corticospinal tracts and motor cortex using a sequence with ISI varying between 1 and 1.5 seconds and having 70 pulses in 7 different amplitudes. More accurate measurements would be gained by adding more pulses, e.g., 150 pulses.

Also the ISI 19 can be irregular, where the ISI 19 changes apparently randomly, throughout the sequence within preset limits, e.g., between 1 and 2 seconds. While this randomization does not have to be mathematically perfect, it is satisfactory to have the ISI vary irregularly such that the stimulated person does not learn to expect a pulse to significant amount. For the duration of the pulse 18 is used reference numeral 20. The duration 20 of the pulses 18 varies in the range of approximately 50 microseconds to 2 milliseconds, advantageously from 100 to 500 microseconds. In accordance with the invention the duration 20 of the pulse 18 may vary within the sequence 17.

The irregular stimulation sequences differ greatly from the previously used repetitive TMS (rTMS) sequences where the train of pulses consists of pulses of equal intensity. This is true also for so-called theta-burst TMS, where the rTMS sequence is broken into shorter blocks with waiting interval between the blocks. On the contrary, irregular sequences include pulses of varying amplitude, where the intensity varies within a preset range of amplitudes. Although the amplitude can vary between the minimum and the maximum of the stimulator output amplitude, normally a smaller range of amplitudes is used.

The previously known repetitive TMS trains have always a fixed ISI, normally from 20 milliseconds to 1 seconds. On the other hand, in irregular pulse sequences, irregularity can be further increased by varying the inter-stimulus interval, for example, between 1 and 2 seconds. Also shorter ISI values can be used to achieve shorter duration of the pulse sequence.

Irregular pulse sequences can be formed by a data processor, or a computer. The sequences can also be precalculated, and the user can load them into the memory of the device for execution. Otherwise, sequence can be calculated by the device software. The pulse sequence execution is then controlled by the device software and control electronics.

The pulse sequence here described is applied together with a detection, observation, or measurement of response to each of the pulses. Also this differs greatly from those existing pulse trains or rTMS that are used to interfere with the brain's processing or to generate an effect that has the goal of modulating or changing the brain functions.

An irregular TMS pulse sequence is designed that has N pulses, each of intensity $A_i$ and given at time $t_i$ (i=1, ..., N):

$$S_i(A_i,t_i), i=1, \ldots, N,$$

Where intensity $A_i$ and $t_i$ are varied according to a predesigned plan. Since the brain's reaction to a TMS pulse may partially be modulated by one or more previous pulses, it is preferred to design the sequence such that the $A_i$ are randomized, rather than giving the stimuli, for instance, ordered by increasing intensity.

Biological measurable changes elicited by each pulse are recorded simultaneously. A beneficial measurement is EMG to observe motor-evoked potentials ($R_i$) resulting from muscle twitches. There is a known relationship that when $A_i$ is weak, $R_i$ is zero or close to zero; for strong $A_i$, $R_i$ saturates after approximately 1-15 mV depending on the muscle. The relationship between MEP's and $R_i$ is generally S-curve shaped. It is notable that although there is a general S-curve-shaped dependency, the same $A_i$ does not always cause the same MEPi, but the relationship is known to have remarkable statistical variation.

It is preferable to vary $t_i$ randomly because an evenly repeated stimulus can cause habituation in the brain and the subject learns quickly to expect a stimulus, which can change the brain's responsiveness to the stimulus.

The following benefits are identified. By choosing $A_i$ such that in a train of N pulses, an intensity $A_i$ repeats several times, it is possible to compute average $R_i$ to different $A_i$. By choosing at least 2, but optimally at least 5 categories of intensities $A_i$, it is possible to form an estimate the relationship between $A_i$ and $R_i$.

TMS studies frequently determine the so-called motor threshold (MT). MT is defined as the stimulus intensity that will elicit MEP's with value greater than or equal to 50 µV to half of the stimuli and less than 50 µV to half of the stimuli. Due to the statistical nature of MEP's the, determining the absolute value of MT would in theory require an infinite number of stimulus pulses.

Irregular pulse sequences allow for non-iterative determination of the MT. This is contrary to presently known iterative searches, where the amplitude of a stimulus pulse depends on the response to the previous pulse. In non-iterative MT determination, responses to pulses in an irregular pulse sequence are recorded. Next, the stimulus-response pairs for all pulses in the sequences are fitted to a statistical model for the MEP's, and the MT value is determined. The calculation can make use of parameter estimation by sequential testing (PEST) type of algorithms. The statistical model can be simple probabilistic density function for the actual threshold values when data has been obtained for given assumptions. The cumulative distribution can be normal distribution. Next, one can estimate the expected value of the MT by maximizing the likelihood of a suitable function. Brent-search or other suitable algorithm can be used to maximize the likelihood function.

Summary of an Example Measurement

EMG was recorded with surface electrodes from two muscles: abductor pollicis brevis (APB, thumb) and abductor digiti minimi (ADM, little finger) in the right hand. The stimulator coil was first held over the parietal cortex in the left hemisphere and it was moved in steps to locate a coil location where stimulation could elicit strong MEP's at low stimulation intensity. This coil location and orientation were then recorded.

The TMS stimulator was set to give a pulse train with 70 pulses, containing stimuli of 7 different intensity values (28, 34, 40, 45, 51, 57 and 62% of the maximum output of the stimulator). The order of the stimuli of different intensities was varied randomly. EMG responses to each stimulus were recorded and their latency and peak-to-peak size were determined. Stimuli were given to the coil location that had been previously recorded. Coil was maintained essentially in the same location for all stimulus pulses with the help of a 3D localization device. The pulses were given with an inter-stimulus interval of ca. 2 seconds. The subject was instructed to keep the hand muscles relaxed.

Figure 5:
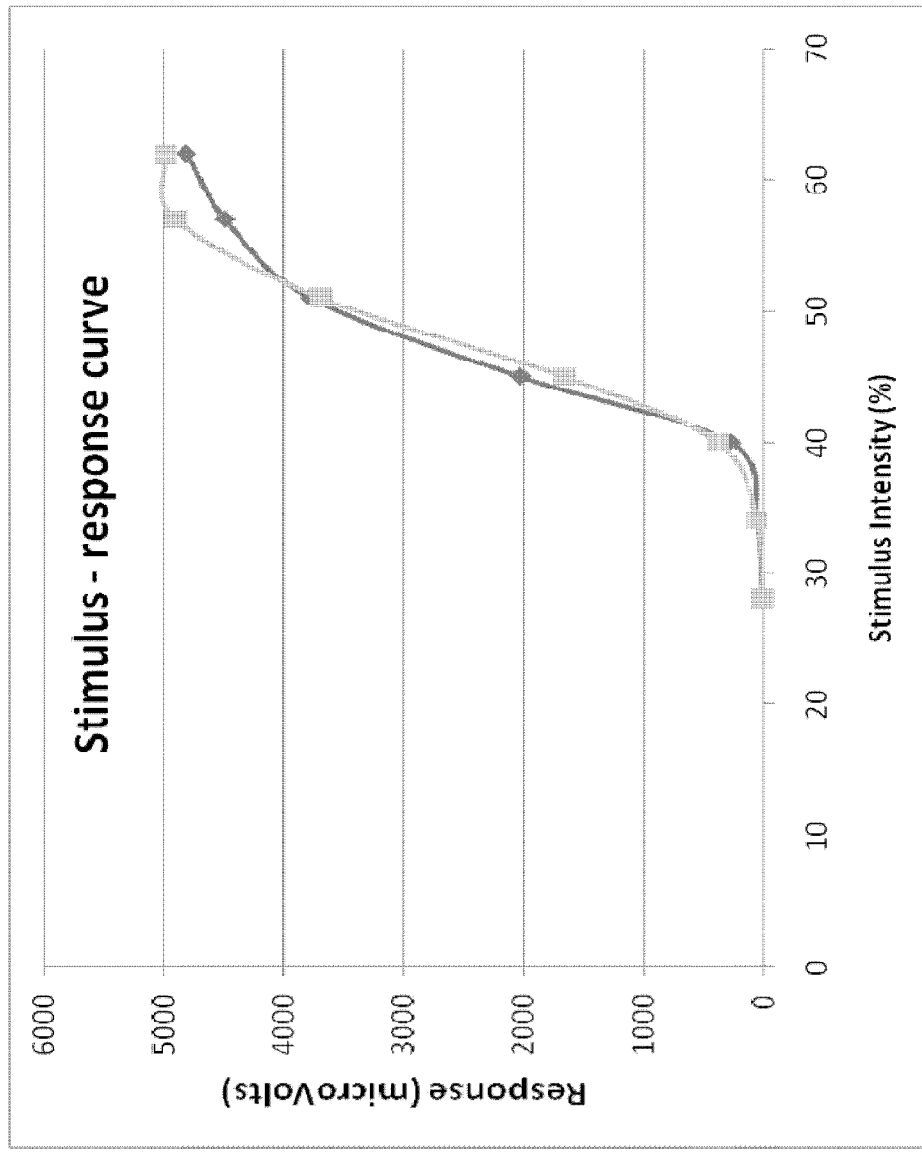
FIG. 5 presents graphically stimulus—response curve, where each marker represents the average of 10 responses. The two curves represent measurements at two days.

After the examination ended, all EMG responses were reviewed for their latency and peak-to-peak size. The following analysis was conducted. The peak-to-peak values to each of the stimulus intensities were averaged (two strongest and two weakest stimuli were excluded and the remaining 6 responses averaged). Standard deviation in each point was calculated. A curve was plotted with the intensity on the x-axis and the mean response size on the y-axis. FIG. 5 shows the resulting curves obtained at two different days.

Figure 6:
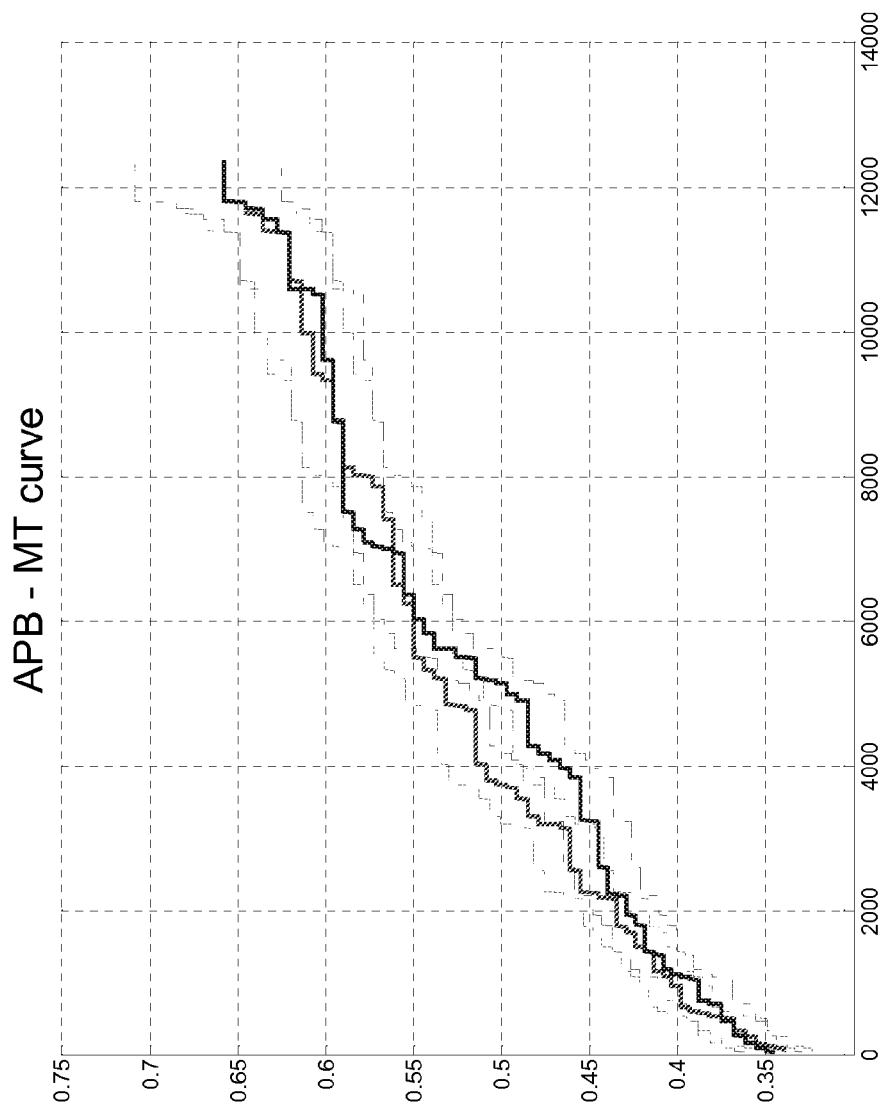
FIG. 6 shows graphically stimulator threshold intensity plotted against the MEP classification limit for Abductor pollicis brevis muscle for one subject.

Next, the MT was determined using maximum likelihood search. In this approach, the statistical variation in the MEP's is modeled as Gaussian distributed. The MT value is derived as the expectation value for the stimulus intensity that would statistically yield responses to 50% of the stimuli. Similar algorithm has earlier been described for the calculation of the next intensity to be given in an iterative search for the MT. Here a variation of the algorithm is used without iteration. Responses with peak-to-peak value equal to a greater than a threshold value were categorized as "response"; weaker responses were categorized as "no-response". Error bounds for the estimation were also calculated. The MT determination was repeated for varying response categorization threshold value from 0 to the peak-to-peak value of the strongest MEP of the 70 pulses. The measurement was conducted on two separate days to demonstrate the repeatability. The results are shown in FIG. 6 where the stimulator intensity is plotted against the MEP classification limit for Abductor pollicis brevis muscle for one subject. The two lines are measurements from two different days; the broken lines are the calculated error bounds. X-axis is the MEP classification limit in microvolts; responses stronger than the limit value are classified as positive responses. On the y-axis are the estimated stimulator intensities that would result in 50% of positive responses and 50% of negative responses at each MEP classification limit value.

Curves presented in FIGS. 5 and 6 can have different shapes depending on the status of the primary motor cortex, other brain areas, and the corticospinal tracts. Low stimulus intensities tend to excite the cortical neurons, while higher stimulus intensities stimulate also directly the corticospinal tract neurons. Connections to other areas of the cortex and the brain can affect the excitability of the stimulated cortex. Thereby the examinations described can include differential information about the state of the different parts of the central nervous system. Day-to-day changes may be helpful in observing trends in the state of the central nervous system.

Further Improvements

Another object of the invention is to use it as an extension of the combined TMS and EMG method for studying the non-motor areas of the brain using EEG measurement instead of EMG.

Some more detailed objects are listed below:

Conditioning pulses can be given prior to irregular pulse sequence. This can be used to stabilize the state of the brain prior to the sequence to further increase reliability and reproducibility of the irregular sequences It may be useful to deliver the sequences at controlled level of preinnervation of the target muscles.

Several recording EMG channels can be combined mathematically to increase the signal-to-noise ratio of the experiments. For instance, if the subject's motor pathway carried by the median nerve is examined, it may be useful to combine the recording signals from several muscles innervated by the median nerve.

Dynamic features (to test how well the cortex adapts eg stroke vs normal, and during recovery from stroke, spinal cord injury, multiple sclerosis, traumatic brain injury etc): deliver $1^{st}$ test sequence, then give a manipulation TMS sequence or use other technique (e.g., motor rehabilitation), $2^{nd}$ test sequence. Compare change and its statistical relevevance.

A modification to the above-described protocol can be that there are, for instance, 70 pulses that all have different intensity, and are delivered in essentially random order. Another modification is that some of the pulses have the same intensity. Instead of 70 pulses, less or more pulses may be used.

An additional modification is that the pulse sequence is adaptive based on essentially real-time analysis of the stimulus-response characteristics in accordance with FIG. 5. This can be performed, for instance, by splitting a pulse sequence in several irregular pulse subsequences. For instance, when the first pulse sequence has repeated a stimulus intensity value for more than 3 times and has resulted in no response, it may be beneficial to remove this intensity value from the list of next stimulus sequence. Likewise, if the responses to one or more stimulus categories is variable (judged, e.g., based on the standard deviation calculated), it may be beneficial to lengthen or add another sequence by including more repetitions at these stimulus intensities.

Another modification is that instead of using the intensity value expressed in terms of the percentage of the stimulator's maximum value, the intensity is expressed as the strength of the electric field induced in a selected point inside the brain (see, e.g., Ilmoniemi et al., Crit. Rev. Biomed. Eng., 27: 241-284, 1999), or in terms of the estimated change in the neuronal membrane potential in the selected locations, calculated based on the induced electromagnetic field, its temporal waveshape, and the cells' approximated membrane and shape characteristics.

Predefined pulse sequence that contains in randomized (or pseudo-randomized) train of pulses of varying intensities with one or more pulse in each intensity, where the response values are averaged (if more than one pulse in category) and their relationship with intensity is further processed, and where the responses are categorized in at least two categories based on response size, and where the categories are fed to an algorithm that calculates a threshold intensity for the change from one category to another.

In one preferred embodiment the device in accordance with the invention includes means for controlling a temporary energy resource, like a capacitor for generating short, high energy current pulses 18 in order to create the next pulse in the pulse sequence 17. Typically this feature is needed when in the sequence 17 a low energy pulse follows a high energy pulse. This problem is solved by the invention by connecting to the capacitor at least a switch and a resistor that allow for controllably releasing the energy from the capacitor through the resistor into the ground for the low energy pulse. The solution can include a means for measuring the capacitor charging level and a feedback loop between the discharging circuitry and the level of the remaining charge. The resistors should be chosen such that they withstand without breaking several discharges of the capacitor from relatively high level to relatively low level. It may be useful to add cooling for the resistors. It is also possible to replace at least part of the resistors using another capacitor bank where the excessive energy is transferred and from where the energy can be returned to the pulse-generation circuit's capacitor in order to reduce need for mains power.

The invention claimed is:

1. A device for generating magnetic pulses and directing them to a brain of a subject, the device comprising:
   means for generating short, high energy current pulses;
   means for controlling amplitude of the current pulses;
   means for generating high energy electromagnetic field stimulation pulses from the current pulses and directing the generated stimulation pulses to the brain of the subject;
   means for determining biologic responses to the directed stimulation pulses;
   means for creating a predetermined pulse sequence of electromagnetic field stimulation pulses where an amplitude of the pulses in the pulse sequence varies irregularly; and
   means for determining, non-iteratively, a motor threshold (MT) based on responses to the predetermined pulse sequence.

2. A device in accordance with claim 1, wherein the means for determining biologic responses includes also means for measuring the biologic responses to the directed stimulation pulses.

3. A device in accordance with claim 1, including localization means for defining one or more of location, direction, and magnitude of a directed electromagnetic pulse.

4. A device in accordance with claim 1, wherein the pulse sequence is directed without any feedback from the biologic responses to the directed stimulation pulses.

5. A device in accordance with claim 1, further including means for adapting the created sequence based on the feedback from the responses to the stimulation.

6. A device in accordance with claim 5 the device including:
   a temporary energy resource for generating the short, high energy current pulses; and
   means for charging or discharging the temporary energy resource in order to change the amplitude of a pulse defined by the amplitude of a next pulse in the pulse sequence.

7. A device in accordance with claim 1, including means for calculating relationship between the pulse sequence and the corresponding determined biologic responses.

8. A device in accordance with claim 7, the device further including:
   means for generating a signal or message that includes a stimulus intensity associated with at least one directed pulse and the determined biologic response to said at least one directed pulse; and
   means for outputting the results of programmed calculation from two or more such signals or messages, which calculation provides estimates of the relation between the stimulus intensity and the determined biologic response characteristics.

9. A device in accordance with claim 7, including means for forming motor threshold based on the pulse sequence and corresponding determined biologic responses.

10. A device in accordance with claim 1, including means for adjusting a time between pulses within the sequence such that the time between pulses within the sequence is irregular.

11. A device in accordance with claim 1, including means for adjusting irregular durations for two or more pulses within the created pulse sequence.

12. A device in accordance with claim 1, including means for expressing a pulse intensity of a pulse within the sequence in terms of an electric field induced in the brain or a quantity derived from the induced electric field.

13. A device in accordance with claim 1, including means for detecting a status of the subject; and
   means for pausing the execution of the stimulation sequence if the detected status is outside limits set by an operator or a control system.

14. A device in accordance with claim 1, including means or performing calculations after the execution of the entire pulse sequence that estimate the relation between the stimulus pulses and the responses, the performed calculations relating to one or more of motor threshold, and motor recruitment curve.

15. A device in accordance with claim 1, including means for performing calculation after direction of the pulse sequence to the brain to estimate a threshold stimulation intensity to elicit responses of different amplitudes.

16. A device in accordance with claim 1, including means for performing calculations during direction of the pulse sequence to the brain and using the biologic responses determined during pulse direction to change one or more of an intensity, an interstimululs interval, and a remaining number of pulses in the sequence before the sequence is ended.

17. A device in accordance with claim 1, including means for localizing the determined biologic response with respect to images acquired using one or more of Computed Tomography, Magnetic Resonance Imaging, or Ultrasound of the subject.

18. A device in accordance with claim 1, including means for measuring biosignals by an electromyography device.

19. A device in accordance with claim 1, including means for measuring biosignals using an electroencephalography device.

20. A device in accordance with claim 1, including means for comparing results of direction of the created pulse sequence to results of a previous direction of a previously-created pulse sequence to the subject.

21. A device in accordance with claim 1, including means for automating direction of the created sequence and calculation of output results.

22. A device in accordance with claim 1, including means for comparing results to results obtained from a different muscle, either previously or simultaneously, of the same subject.

23. A method for generating magnetic pulses and directing them to a brain of a subject, the method comprising the following steps:
generating short, high energy current pulses;
controlling amplitude of the generated current pulses;
generating high energy electromagnetic field stimulation pulses from the generated current pulses;
directing the generated stimulation pulses to the brain of the subject;
determining biologic responses to the directed stimulation pulses;
creating a predetermined pulse sequence of electromagnetic field stimulation pulses where an amplitude of the pulses in the pulse sequence varies irregularly; and
determining a motor threshold (MT) non-iteratively based on responses to the predetermined pulse sequence.

24. A method in accordance with claim 23, including measuring the biologic responses to the directed stimulation pulses.

25. A method in accordance with claim 23, including defining one or more of location, direction, and magnitude of a directed electromagnetic pulse.

26. A method in accordance with claim 23, the step of directing including directing the pulse sequence without any feedback from the biologic responses elicited during said directing.

27. A method in accordance with claim 23, including adapting the created sequence during said directing based on the feedback from the biologic responses elicited during said direction.

28. A method in accordance with claim 23, said generating short, high energy pulses including:
using temporary energy resource to generate the short, high energy current pulses by controlling charging and discharging of the temporary energy resource in order to change the amplitude of a pulse defined by the amplitude of a next pulse in the pulse sequence.

29. A method in accordance with claim 23, including calculating a relationship between the directed pulse sequence and the corresponding determined biologic responses.

30. A method in accordance with claim 29, including
generating a signal or message that includes a stimulus intensity of at least one directed pulse and the determined biologic response to the at least one directed pulse; and
outputting results of programmed calculation from two or more said generated signals or messages, the programmed calculation providing estimates of a relation between the stimulus intensity and the determined biologic response characteristics.

31. A method in accordance with claim 29, including forming motor threshold based on the directed pulse sequence and corresponding biologic responses.

32. A method in accordance with claim 23, including adjusting a time between pulses within the created pulse sequence such that the time between pulses is irregular.

33. A method in accordance with claim 23, including adjusting irregular durations for two or more pulses within the created pulse sequence.

34. A method in accordance with claim 23, including expressing a pulse intensity of one or more pulses in the created pulse sequence in terms of an electric field induced in the brain or a quantity directly related to the electric field.

35. A method in accordance with claim 23, including:
detecting a status of the subject; and
pausing said directing of the sequence if the detected status is outside limits set by an operator or a control system.

36. A method in accordance with claim 23, including performing calculations after the directing of the entire sequence, the step of performing calculations including estimating a relation between the directed stimulus pulses and the determined biologic responses.

37. A method in accordance with claim 23, including performing a calculation after the step of directing to estimate a threshold stimulation intensity to elicit responses of different amplitudes.

38. A method in accordance with claim 23, including performing calculations during the step of directing and
using results the performed calculations to change one or more of an intensity, an interstimululs interval and a remaining number of pulses still to be given during said directing before the sequence is ended.

39. A method in accordance with claim 23, including localizing the determined biologic response with respect to computed tomography (CT) or magnetic resonance (MR) images of the subject.

40. A method in accordance with claim 23, including measuring biosignals by an electromyography.

41. A method in accordance with claim 23, including measuring biosignals using an electroencephalograph.

42. A method in accordance with claim 23, including comparing results of said directing to results of a previous directing of a previously-created pulse sequence to the subject.

43. A method in accordance with claim 23, including automating said delivering; and
automating calculation of output results.

44. A method in accordance with claim 23, including comparing results to previously obtained results of the same subject.

45. A non-transitory computer-readable medium having embodied thereon instructions which, when executed by a computer, cause the computer to perform control of a method of generating magnetic pulses and directing them to a brain of a subject, the method comprising the following steps:
controlling generation of short, high energy current pulses;
controlling amplitude of the generated current pulses;
controlling generation of high energy electromagnetic field stimulation pulses from the generated current pulses;
directing the generated stimulation pulses to the brain of the subject;
determining biologic responses to the directed stimulation pulses;
creating a predetermined pulse sequence of electromagnetic field stimulation pulses where an amplitude of the pulses in the pulse sequence varies irregularly; and
determining a motor threshold (MT) non-iteratively based on responses to a predetermined pulse sequence.

* * * * *